US009121916B2

(12) United States Patent
Wang et al.

(10) Patent No.: US 9,121,916 B2
(45) Date of Patent: Sep. 1, 2015

(54) METHOD AND APPARATUS FOR SCANNING CONTROL AND DISPLAYING IMAGES IN A MAGNETIC RESONANCE SCANNING CHAMBER

(75) Inventors: Yong Wang, Shenzhen (CN); Zanchao Zhang, Shenzhen (CN); Zhaoquan Liu, Shenzhen (CN); Haitao Tong, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 278 days.

(21) Appl. No.: 13/181,815

(22) Filed: Jul. 13, 2011

(65) Prior Publication Data

US 2012/0089011 A1    Apr. 12, 2012

(30) Foreign Application Priority Data

Oct. 12, 2010    (CN) .......................... 2010 1 0512440

(51) Int. Cl.
*G01R 33/54* (2006.01)
*A61B 5/055* (2006.01)
*A61B 5/00* (2006.01)

(52) U.S. Cl.
CPC .............. *G01R 33/543* (2013.01); *A61B 5/004* (2013.01); *A61B 5/0046* (2013.01); *A61B 5/055* (2013.01); *A61B 5/0555* (2013.01); *G01R 33/546* (2013.01)

(58) Field of Classification Search
CPC .... G01R 33/543; G01R 33/546; A61B 5/004; A61B 5/0046; A61B 5/055; A61B 5/0555
USPC .......................................... 600/410, 422, 415
See application file for complete search history.

(56) References Cited

U.S. PATENT DOCUMENTS

| 6,195,409 B1* | 2/2001 | Chang et al. ..................... 378/20 |
| 6,934,574 B1* | 8/2005 | Damadian et al. ............ 600/415 |
| 2003/0018250 A1* | 1/2003 | Trousset et al. ............... 600/425 |
| 2003/0135103 A1 | 7/2003 | Mistretta |
| 2007/0167724 A1 | 7/2007 | Gadagkar et al. |
| 2007/0185395 A1* | 8/2007 | Glaser-Seidnitzer et al. 600/410 |
| 2009/0234218 A1* | 9/2009 | Washburn et al. ............ 600/410 |
| 2009/0259121 A1 | 10/2009 | Simonetti et al. |

\* cited by examiner

*Primary Examiner* — Katherine Fernandez (74) *Attorney, Agent, or Firm* — Kory D. Christensen; Stoel Rives LLP (57) ABSTRACT

A method and apparatus for scanning control and displaying an image in a magnetic resonance scanning chamber are disclosed. An apparatus includes a magnetic resonance imaging system, a scanning chamber computer, an operating chamber computer, and a communication connection device; the scanning chamber computer and the magnet are disposed in the scanning chamber together; the operating chamber computer is disposed in the operating chamber; the scanning chamber computer and the operating chamber computer are connected via the communication connection device.

6 Claims, 7 Drawing Sheets

METHOD AND APPARATUS FOR SCANNING CONTROL AND DISPLAYING IMAGES IN A MAGNETIC RESONANCE SCANNING CHAMBER

CROSS-REFERENCE TO RELATED APPLICATION(S)

This application claims the benefit of Chinese Patent Application No. 201010512440.7, filed on Oct. 12, 2010, which is incorporated herein by reference in its entirety.

TECHNICAL FIELD

The following disclosure generally relates to magnetic resonance imaging, and more particularly, to a method and an apparatus for scanning control and displaying an image in a magnetic resonance scanning chamber.

DETAILED DESCRIPTION

A magnetic resonance scan generally includes several steps, such as patient registration, positioning the patient (coil connection), positioning scan, and general scan. A magnetic resonance system is generally distributed in three chambers: a scanning chamber, a device chamber, and an operating chamber. Since a computer or the like may generate electromagnetic interference, an operating device, such as computer, cannot be placed into the scanning chamber. This causes the operations of positioning the patient and scanning control to be respectively performed in the scanning chamber and the operating chamber.

Such a configuration results in the following problems. If there is a relatively large deviation in a patient's swaying position, after the patient has been positioned, an operator has to go out of the scanning chamber, initiate a localizer scan (i.e., scouting scan), review a positioning image, and then come into the scanning chamber again to readjust the patient's swaying position. Typically, a localizer scan is first performed to produce relatively low-quality images, as known in the art, to assist the operator of an MRI machine in deciding, for example, whether the machine is functioning normally, whether the patient is properly positioned, where any metal artifacts exist, etc.

A similar condition will occur during imaging for moving targets, i.e., each time after a scan is finished, an operator needs to come into the scanning chamber again, adjust the position of a coil, go back to the operating chamber, and perform a next scan.

When using a contrast agent, two operators are needed to accomplish the process, that is, after one operator injects the contrast agent, the other operator initiates the scan.

During an interventional surgery treatment, an operator needs to go out of the scanning chamber, and come into the operating chamber to initiate a next scan, while the surgery process is going on.

When a particular patient who needs nursing care is scanned, it is necessary that several medical personnel cooperate with each other so as to accomplish the scan operation.

The above problems elongate the scanning process for each patient and affect the comfort of a patient and the efficiency of an apparatus.

To address these problems, a method and apparatus for scanning control and displaying images in a magnetic resonance scanning chamber is provided. In one embodiment, a method for scanning control in a magnetic resonance scanning chamber includes the following steps:

determining an examination body part of a patient, selecting a radio frequency receiving coil corresponding to the examination body part, making the patient enter into a magnet apparatus and reaching a specified position when the patient is in position on a examination bed;

sending a request for initiating a positioning scan by a scanning chamber computer, wherein the request is sent to an operating chamber computer via a communication connection device;

selecting a corresponding localizer protocol by the operating chamber computer on the basis of the currently selected examination body part or the automatically detected type of the radio frequency receiving coil, and then initiating a scan;

scanning the patient, and transferring echo signals obtained from the scanning to the operating chamber computer for reconstruction so as to obtain positioning images.

An apparatus for scanning control in a magnetic resonance scanning chamber, comprises:

a magnetic resonance imaging system for scanning a patient and receiving echo signals;

a scanning chamber computer for sending a request for initiating a scan, performing a queue management operation and displaying an image;

an operating chamber computer for selecting a corresponding scan protocol, then enabling the magnetic resonance imaging system to scan, and reconstructing echo signals obtained from the scanning to obtain positioning images;

a communication connection device for establishing a communication connection for the scanning chamber computer and the operating chamber computer, wherein the scanning chamber computer and the magnet are placed in the scanning chamber together; the operating chamber computer is placed in the operating chamber; the scanning chamber computer and the operating chamber computer are connected via the communication connection device.

The disclosed scanning control method and apparatus effectively solves the inference to magnetic resonance imaging caused by a computer and a display system. A computer may be added in the scanning chamber of a magnetic imaging system, in which the scanning control is achieved, including the functions of scan positioning, scan protocol selection, scan queue management, image displaying etc., and synchronization with the operating chamber computer, thereby providing a real, complete bedside scanning control.

Figure 1:
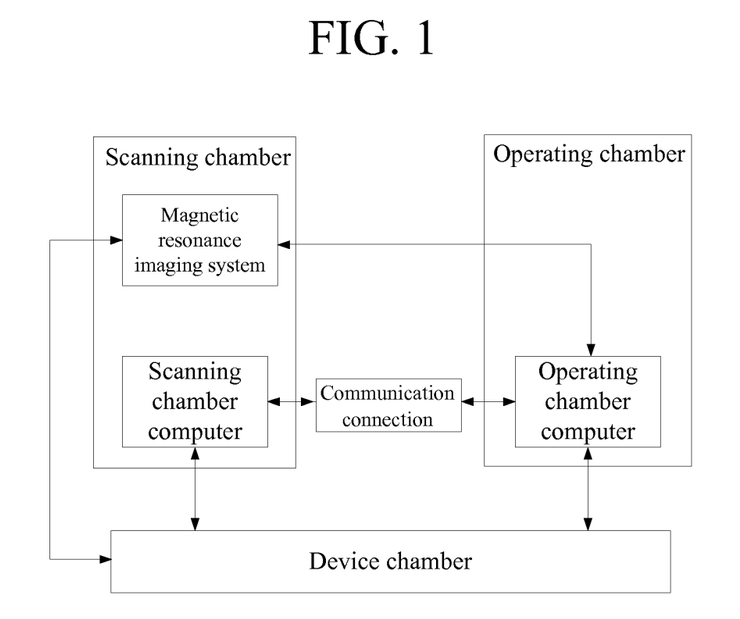
FIG. 1 is a block diagram of a hardware system in accordance with an embodiment of the present disclosure.

Referring to FIG. 1, a hardware system includes a magnetic resonance imaging system, a scanning chamber computer, an operating chamber computer and a communication connection device there between. The magnetic resonance imaging system is used for scanning a patient and receiving echo signals; the scanning chamber computer is used for sending a request for initiating a scan, performing a queue management operation, and displaying images; the operating chamber computer is used for selecting a corresponding scan protocol and then enabling the magnetic resonance imaging system to scan, and reconstructing obtained echo signals to obtain positioning images; the communication connection device is used for establishing a communication connection for the scanning chamber computer and the operating chamber computer.

In one embodiment, the scanning chamber computer employs a industrial control computer (IPC), and its screen employs an LCD and a touch panel. The scanning chamber computer and the magnet are placed in the scanning chamber together. The operating chamber computer employs a normal desktop computer, which is placed in the operating chamber. The scanning chamber computer and the operating chamber computer are connected via a communication connection device, which may utilize optical fiber transmission.

After a patient enters into the magnet, the scanning chamber computer determines the body part to be examined on the basis of the patient's registration, and selects a receiving coil. After the patient is in position, the scanning chamber computer sends a request for a localizer scan to the operating chamber computer. The operating chamber computer automatically selects a localizer protocol on the basis of the receiving coil or the selected examination body part, then selects an protocol and parameters and initiates a scan. The magnetic resonance imaging device scans a specific part of the patient according to the protocol, and transfers received echo signals to the operating chamber computer for reconstructing positioning images. Finally, the operating chamber computer transfers the obtained positioning images to the scanning chamber computer via the communication connection device, and the positioning images are displayed on the LCD of the scanning chamber computer.

By means of the above apparatus, the localizer operation is performed in the scanning chamber, thereby accomplishing bedside scanning control of magnetic resonance examination in a true sense. In one embodiment, the apparatus performs three functions as follows:

1. Enabling a Localizer Scan in a Scanning Chamber.

The request for enabling a localizer scan is initiated from the scanning chamber, the request is sent to the operating chamber computer via the communication connection, the operating chamber computer selects a corresponding localizer protocol on the basis of the currently selected examination body part or the automatically detected receiving coil, and initiates a scan. After the scan is finished, positioning images are reconstructed and obtained, and they are transferred to the scanning chamber computer via the communication connection device. Eventually the positioning images are displayed on a display screen by means of the scanning chamber computer, thereby finishing the process of the localizer scan.

2. Selecting a Scan Protocol and Managing a Queue in the Scanning Chamber.

When managing a scan queue, the scanning chamber computer will first request the operating chamber computer for the following information: part information, examination information, protocol group information, protocol information, etc. All the operations will be provided to the operating chamber computer via the communication connection device. When an operation of managing a scan queue (including adding or deleting protocols) is performed, the operating chamber computer is informed, ensuring that information is synchronized on both sides.

Radiologists have certain images they like to see for each type of investigation, typically, but not necessarily, in a standard order. As used herein, a "scan protocol" is a set of examination parameters used to finish a scan. A "scan protocol group" is a group of scan protocols recommended for a particular region being investigated. A "scan protocol queue" is the set of scan protocols selected for scanning.

3. Instantly Initiating a Scan in the Scanning Chamber.

While performing a positioning operation in the scanning chamber, modified geometry parameters are calculated according to the positioning operation and are sent to the operating chamber computer, and the geometry parameters displayed on the operating chamber computer are synchronously modified.

Thereafter, the following operations are performed: initiating a scan in the scanning chamber, initiating the scan on the basis of the selected scan queue, sending a scan request from the scanning chamber computer to the operating chamber computer via a communication connection, performing the scanning and reconstructing by the operating chamber computer, displaying images that are sent to the scanning chamber computer.

Figure 2:
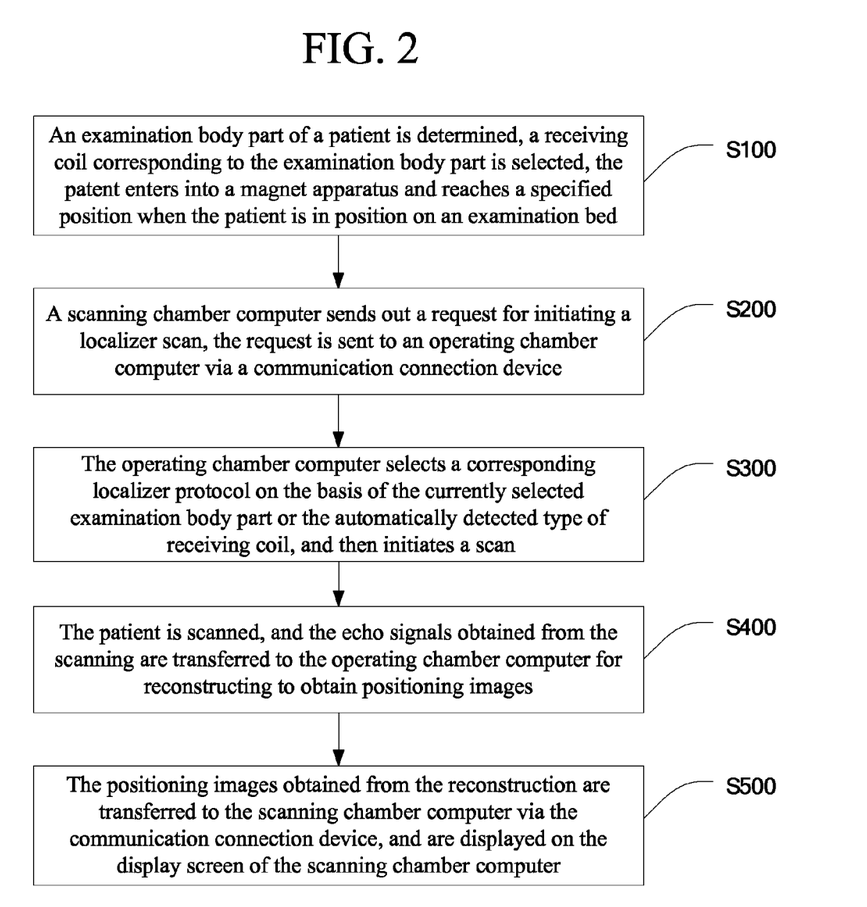
FIG. 2 is a flow chart of a method in accordance with an embodiment of the present disclosure.

The above-described devices are employed to perform a method for positioning scan control in the scanning chamber. As shown in FIG. 2, the method flow includes the following steps:

Step S100: An examination body part of a patient is determined, a receiving coil corresponding to the examination body part is selected, the patient enters into the magnet and reaches a specified position when the patient is in position on a examination bed;

Step S200: A scanning chamber computer sends out a request for initiating a localizer scan, the request is sent to an operating chamber computer via a communication connection device;

Step S300: After receiving the request for initiating the scan, the operating chamber computer selects a corresponding localizer protocol on the basis of the currently selected examination body part or the automatically detected type of receiving coil, and then initiates a scan;

Step S400: The patient is scanned, and echo signals obtained from the scanning are transferred to the operating chamber computer for reconstructing to obtain positioning images;

Step S500: The positioning images obtained from the reconstruction are transferred to the scanning chamber computer via the communication connection device, and are displayed on the display screen of the scanning chamber computer.

Figure 3:
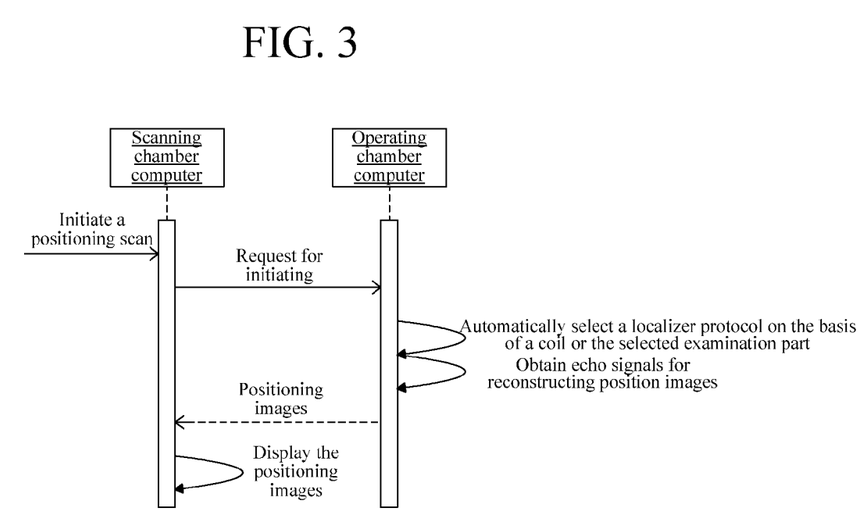
FIG. 3 is a timing chart of initiating a localizer scan in a scanning chamber.

The timing sequence of the positioning scan is shown in FIG. 3. The request for initiating the positioning scan is initiated from the scanning chamber. The request is sent to the operating chamber computer via a communication connection. The operating chamber computer selects a corresponding localizer protocol on the basis of the currently selected examination body part or the automatically detected receiving coil, and initiates a scan. After the scan is finished, the positioning images are reconstructed and obtained, and they are transferred to the scanning chamber computer via the communication connection device. Eventually the positioning images are displayed on the display screen by means of the scanning chamber computer, and then the process of the positioning scan is finished.

Figure 4:
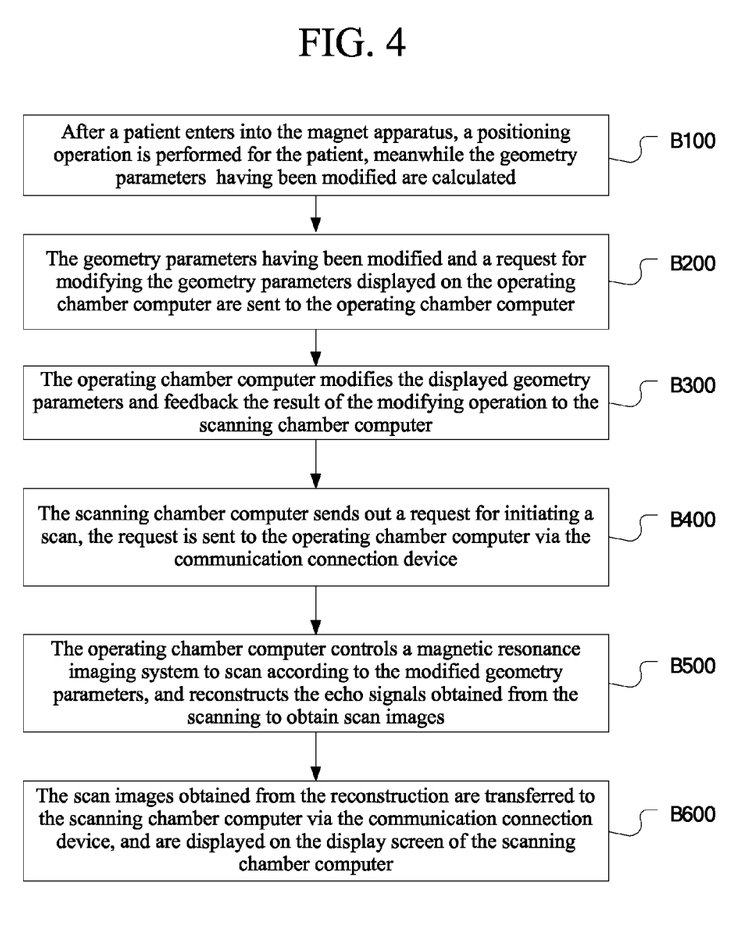
FIG. 4 is a flow chart of a method for instantly initiating a scan in a scanning chamber.

When the above apparatus is employed to perform a general scan, the following operations can also be performed on the scanning chamber computer: performing a positioning operation, determining geometry parameters, and instantly initiating a scan. A flowchart of a method for such operations is shown in FIG. 4, which comprises the following steps:

Step B100: After a patient enters into the magnet, a positioning operation is performed for the patient, the geometry parameters having been modified are calculated;

Step B200: The geometry parameters having been modified and a request for modifying the geometry parameters displayed on the operating chamber computer are sent to the operating chamber computer;

Step B300: The operating chamber computer modifies the displayed geometry parameters and provides the result of the modifying operation to the scanning chamber computer;

Step B400: The scanning chamber computer sends a request for initiating a scan, and the request is sent to the operating chamber computer via the communication connection device;

Step B500: The operating chamber computer controls a magnetic resonance imaging system to scan according to the modified geometry parameters, and reconstructs echo signals obtained from the scanning to obtain scan images;

Step B600: The scan images obtained from the reconstruction are transferred to the scanning chamber computer via the communication connection device, and are displayed on the display screen of the scanning chamber computer.

Figure 5:
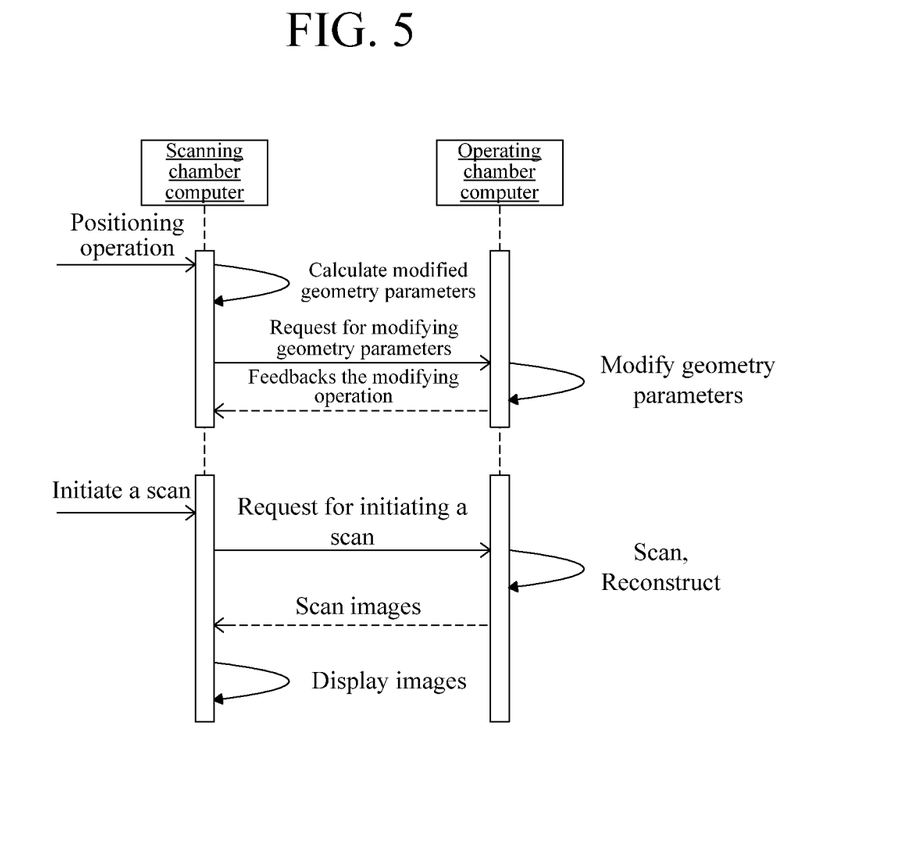
FIG. 5 is a timing chart of instantly initiating a scan in a scanning chamber.

The operation sequence of this method is shown in FIG. 5. While the positioning operation is being performed in the scanning chamber, the modified geometry parameters are calculated according to the positioning operation and sent to the operating chamber computer, and the geometry parameters displayed on the operating chamber computer are modified synchronously. Thereafter, the following operations are performed: initiating a scan in the scanning chamber, initiating the scan on the basis of the selected scan queue, the scanning chamber computer sending a scan request to the operating chamber computer via a communication connection, the operating chamber computer performing the scanning and reconstructing, the scan images are sent to the scanning chamber computer for displaying.

Figure 6:
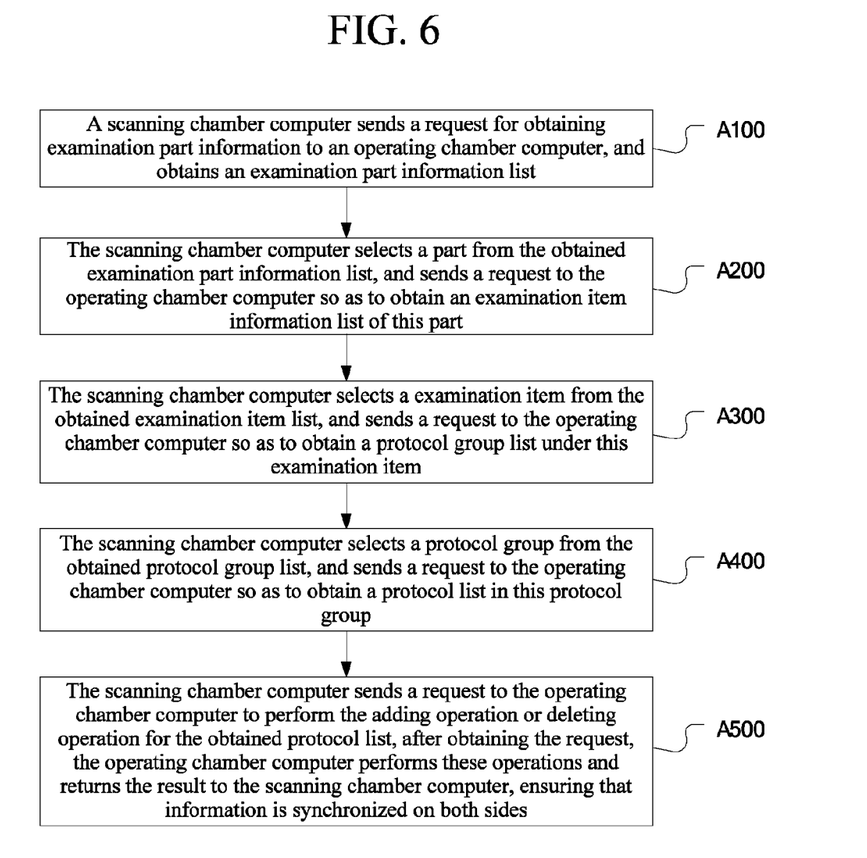
FIG. 6 is a flow chart of a method for selecting a scan protocol and managing a queue in a scanning chamber.

Before performing a localizer scan or general scan, the scanning chamber computer can also manage a scan protocol queue, a flow of a method for such a operation is shown in FIG. 6, including the following steps:

Step A100: A scanning chamber computer sends a request for obtaining examination body part information to an operating chamber computer, and obtains an examination body part information list;

Step A200: The scanning chamber computer selects a part from the obtained examination body part information list, and sends a request to the operating chamber computer so as to obtain an examination item information list of this part;

Step A300: The scanning chamber computer selects a examination item from the obtained examination item list, and sends a request to the operating chamber computer so as to obtain a protocol group list under this examination item;

Step A400: The scanning chamber computer selects a protocol group from the obtained protocol group list, and sends a request to the operating chamber computer so as to obtain a protocol list in this protocol group;

Step A500: The scanning chamber computer sends a request to the operating chamber computer to perform the adding operation or deleting operation for the obtained protocol list, and, after obtaining the request, the operating chamber computer performs these operations and returns a result to the scanning chamber computer, ensuring that information is synchronized on both sides.

Figure 7:
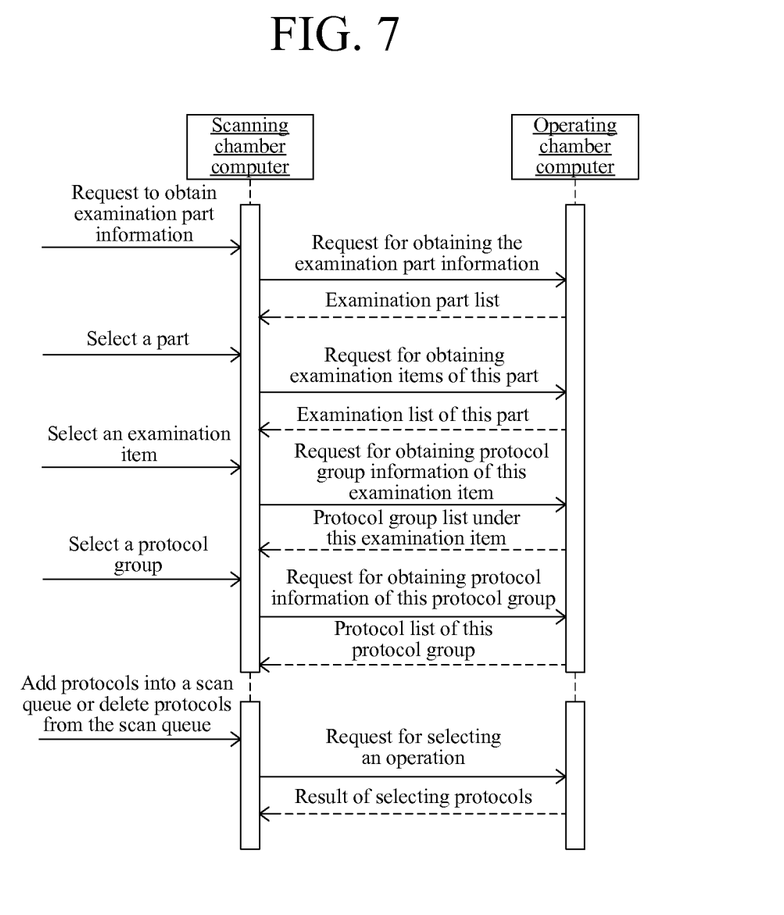
FIG. 7 is a timing chart of selecting a scan protocol and managing a queue in a scanning chamber

The timing sequence for managing the scan protocol queue is shown in FIG. 7. When managing the scan queue, the scanning chamber computer will first request to the operating chamber computer for the following information: part information, examination information, protocol group information, protocol information etc. All the operations will be informed to the operating chamber computer via the communication connection device. When managing the scan queue (including adding or deleting protocols), such an operation will also be provided to the operating chamber computer, ensuring that information is synchronized on both sides.

The present disclosure also provides a method for performing a magnetic resonance imaging in a scanning chamber. The method may include the following steps:

Step 1, after a magnetic resonance imaging system receives a request for initiating a scan, a patient is scanned, and the received echo signals are delivered to the operating chamber computer;

Step 2, the operating chamber computer reconstructs the received echo signals, and obtains positioning images or scan images;

Step 3, the positioning images or scan images obtained from the reconstruction are transferred to a display screen disposed in the scanning chamber via the communication connection device.

In the method for performing the magnetic resonance imaging in the scanning chamber, the request for initiating the scan is sent from the scanning chamber, and is sent to the operating chamber computer via the communication connection device.

In one embodiment, an apparatus for performing magnetic resonance imaging in a scanning chamber includes: a magnetic resonance imaging system for scanning a patient and receiving echo signals; a display screen for displaying an image; an operating chamber computer for selecting a corresponding scan protocol, initiating the magnetic resonance imaging system to scan, and reconstructing echo signals obtained from the scanning to obtain positioning images; and a communication connection device for establishing a communication connection for the display screen and the operating chamber computer.

In one embodiment, the display screen and the magnet are placed in the scanning chamber together; the operating chamber computer is placed in the operating chamber; the display screen and an input device are connected with the operating chamber computer via the communication connection device.

The apparatus for performing the magnetic resonance imaging in the scanning chamber further may include: an input device for inputting a request for initiating a scan and a queue management operation. The input device is placed in the scanning chamber, and the input device and the operating chamber computer are connected via the communication connection device.

It should be understood that the scope of the present disclosure is not limited to the above embodiments. Modifications and changes can be made by those skilled in the art. Examples include:

Initiating the positioning scan by a way of automatic operation. For example, after a examination bed reaches a specified position, the localizer scan is automatically started. Alternatively, after the examination bed is in position and stays for a period of time, the localizer scan is automatically initiated.
   There is no computer placed in the scanning chamber.
   There is no computer placed in the scanning chamber, and there are only a display screen and an input device placed in the scanning chamber for implementing the following operations: initiating the localizer scan, performing a scan protocol and scan queue operation, displaying images, performing a positioning operation, and initiating a scan.

An industrial control computer system is not employed in the scanning chamber.

In the scanning chamber, other control systems, such as an embedded system, are employed, on which the following operations are implemented: initiating the localizer scan, performing a scan protocol and scan queue operation, displaying images, performing a positioning operation, initiating a scan, and so on.

In terms of connection device, optical fiber connection device may not be employed, while network cable may be directly employed for connection. Alternatively, a high speed serial interface and CAN communication connection may be employed.

What is claimed is:

1. An apparatus for scanning control in a magnetic resonance scanning chamber, comprising:
   a magnetic resonance imaging system for scanning a patient and receiving echo signals; wherein the magnetic resonance imaging system comprises a magnet which is placed in a scanning chamber;
   a scanning chamber computer placed in the scanning chamber; and
   an operating chamber computer located in an operation chamber separated from the scanning chamber, wherein a communication connection is established between the operating chamber computer and the scanning chamber computer;
   wherein the scanning chamber computer sends a request to the operating chamber computer for initiating a positioning scan, performs a queue management operation on a scan protocol queue received from the operating chamber computer to manage a set of scan protocols selected for scanning, and displays images comprising a positioning image from the positioning scan;
   wherein the operating chamber computer selects a corresponding scan protocol comprising a localizer protocol, initiates the magnetic resonance imaging system to scan in response to the request from the scanning chamber computer, and reconstructs echo signals obtained from the positioning scan to obtain the positioning image;
   wherein the scanning chamber computer also performs a positioning operation during a general scan, wherein the positioning operation comprises selecting a receiving coil corresponding to an examination body part of a patient; wherein the positioning operation further comprises calculating a modified geometry parameter according to the positioning operation and sending a request to the operating chamber computer for modifying a geometry parameter displayed on the operating chamber computer so as to synchronously obtain the modified geometry parameter in the scanning chamber computer and the operating chamber computer; wherein the operating chamber computer initiates the magnetic resonance imaging system to scan according to the modified geometry parameter during the general scan.

2. The apparatus of claim 1, wherein the scanning chamber computer employs an industrial control computer, a screen of which employs an LCD and a touch panel.

3. The apparatus for scanning control according to claim 1, wherein the scanning chamber computer employs an embedded system.

4. The apparatus of claim 1, wherein the system further comprises a communication connection device which uses one of an optical fiber transmission connection, a network cable connection, or a high speed serial interface connection to establish the communication connection between the scanning chamber computer and the operating chamber computer.

5. The apparatus of claim 1, wherein the queue management operation is performed before scanning the patient and the queue management operation comprises:
   sending a request for obtaining examination body part information from the scanning chamber computer to the operating chamber computer;
   obtaining an examination body part information list;
   selecting a part from the obtained examination body part list by the scanning chamber computer;
   sending a request to the operating chamber computer so as to obtain an examination item information list of the selected part;
   selecting an examination item from the obtained examination item list by the scanning chamber computer;
   sending a request to the operating chamber computer so as to obtain a protocol group list under the selected examination item;
   selecting a protocol group from the obtained protocol group list by the scanning chamber computer;
   sending a request to the operating chamber computer so as to obtain a protocol list in the selected protocol group; and
   sending a request to the operating chamber computer by the scanning chamber computer to perform an adding or deleting operation for the obtained protocol list, performing such an operation and returning a result to the scanning chamber computer after the operating chamber computer obtains the request, ensuring that information is synchronized on both sides.

6. An apparatus for scanning control in a magnetic resonance scanning chamber, comprising:
   a magnetic resonance imaging system for scanning a patient and receiving echo signals; wherein the magnetic resonance imaging system comprises a magnet which is placed in a scanning chamber;
   a scanning chamber computer placed in the scanning chamber; and
   an operating chamber computer located in an operation chamber separated from the scanning chamber, wherein a communication connection is established between the operating chamber computer and the scanning chamber computer;
   wherein the scanning chamber computer and the operating chamber computer are arranged to:
   perform a positioning operation during a general scan by the scanning chamber computer; wherein the positioning operation comprises calculating a modified geometry parameter according to the positioning operation and sending a request to the operating chamber computer for modifying a geometry parameter displayed on the operating chamber computer according to the calculated modified geometry parameter;
   modify the displayed geometry parameter and provides a result of the modification to the scanning chamber computer by the operating chamber computer;
   send a request for initiating a scan to the operating chamber computer from the scanning chamber computer;
   initiate the magnetic resonance imaging system to scan according to the modified geometry parameter in response to the request from the scanning chamber computer, and reconstruct echo signals obtained from the scan to obtain a scan image by the operating chamber computer; and transfer the scan image to the scanning chamber computer from the operating chamber computer for displaying the scan image on the scanning chamber computer.

\* \* \* \* \*